United States Patent [19]

Gadelle et al.

[11] Patent Number: 5,578,719

[45] Date of Patent: Nov. 26, 1996

[54] SULPHONATED DERIVATIVES OF CYCLOMALTO-OLIGOSACCHARIDES, THEIR PREPARATION PROCESS AND SUPPORT FOR ACTIVE SUBSTANCES CONTAINING THESE DERIVATIVES

[75] Inventors: Andrée Gadelle, Mont Bonnot; Corinne Bayle, Volvic, both of France

[73] Assignee: Commissariat a l'Energie Atomique, Paris, France

[21] Appl. No.: 242,117

[22] Filed: May 13, 1994

[30] Foreign Application Priority Data

Jun. 3, 1993 [FR] France .................... 93 06654

[51] Int. Cl.$^6$ ............ C07H 5/04; C08B 37/02; C07G 17/00
[52] U.S. Cl. ............ 536/55.1; 536/112; 536/124
[58] Field of Search ................. 536/55.1, 112, 536/124

[56] References Cited

U.S. PATENT DOCUMENTS

| | | | |
|---|---|---|---|
| 3,426,011 | 2/1969 | Parmerter et al. | 260/209 |
| 4,169,079 | 9/1979 | Tabushi et al. | 260/17.4 |
| 4,672,112 | 6/1987 | Matolcsy et al. | 536/46 |

FOREIGN PATENT DOCUMENTS 2669535  5/1992  France .

OTHER PUBLICATIONS

Database WPI, Week 9306, Derwent Publications Ltd., London, GB; AN 93-049640 & JP-A-5 001 102 (Toppan Printing Co. Ltd.) 8 Jan. 1993.

Primary Examiner—John W. Rollins
Attorney, Agent, or Firm—Pearne, Gordon, McCoy & Granger

[57] ABSTRACT

Sulphonated derivatives of cyclomalto-oligosaccharides, their preparation process and support for active substances containing said derivatives.

These derivatives are in accordance with the following formula (I)

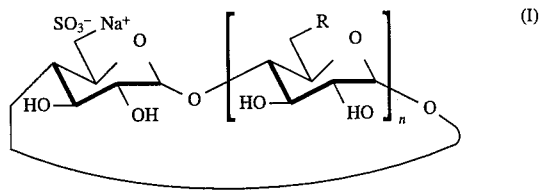

in which n is an integer from 2 to 50 and R represents —SO$_3^-$Na$^+$ or —OH, in which R can differ from one cycle to the other. They can be used for transporting injectable or ingestable medicaments.

10 Claims, No Drawings

SULPHONATED DERIVATIVES OF CYCLOMALTO-OLIGOSACCHARIDES, THEIR PREPARATION PROCESS AND SUPPORT FOR ACTIVE SUBSTANCES CONTAINING THESE DERIVATIVES

DESCRIPTION

The present invention relates to novel derivatives of cyclomalto-oligosaccharides, their preparation process, as well as to a support for active substances containing these derivatives.

More specifically, the invention relates to anionic cyclomalto-oligosaccharide derivatives obtained by fixing a sulphonate group to at least one of the carbons in the 6-position of the cyclic oligosaccharide.

Cyclomalto-oligosaccharides, more widely known as cyclodextrins, are cyclic oligosaccharides of D-glucose usually having six to eight D-glucopyranosyl units linked by the $\alpha$-(1→4) linkages, which gives them a toroidal morphology. As a result of this molecular geometry and the afferent electronic structures, a hydrophobic character is associated with the internal cavity of the cycle, whereas the outer surface of the molecule is hydrophilic.

This arrangement favours the formation of inclusion complexes with hydrophobic molecules by apolar association, thus improving the solubilization of these molecules in water. Thus, cyclodextrins are used for stabilizing unstable molecules, for improving the molecular transport of substances or active principles to target sites, or for aiding interface reactions, as described in document (1), Drug Development and Industrial Pharmacy, 12, 11–13, pp. 2193–2216, 1986.

These properties are extensively used in numerous fields such as the pharmaceutical, veterinary, chemical, agrochemical, food and cosmetic fields, including fragrancies and perfumes.

It is known that the solubility of cyclodextrins in water and therefore that of their inclusion products are significantly increased when the molecule is substituted by hydrophilic groups. This is in particular the case with cyclodextrins having charged polar groups (aminated or sulphated).

In addition, cyclodextrins having a sulphate group have a lower hemolytic activity than that of their unsulphated homologs, as described in document (2), Biochemical Pharmacology, vol. 42, No. 7, pp. 1502–1503, 1991 "Sulfation and hemolytic activity of cyclodextrin" by E. J. Macarak.

Thus, the novel derivatives of cyclomalto-oligosaccharides according to the invention can be used in all known applications of cyclodextrins and particularly as an encapsulating agent and/or agent for transporting active substances insoluble in water such as AZT (C and EN Rudy Baum and R. Dagami, 16/07/1990, pp. 7–15) for the treatment of AIDS.

They can also be used as a complexing agent for cations, e.g. for the extraction of uranyl ions ($UO_2^{2+}$) by replacing the sulphonated calixarenes, as described in document (3), S. Shinkai et al., J. Am. Chem. Soc. 1987, 109, pp. 6371–6376, "Molecular design of calixarene-based uranophiles which exhibit remarkably high stability and selectivity". Thus, the derivatives according to the invention can also be used in the nuclear field for the decontamination of liquid effluents.

Cyclodextrins having anionic properties are also described in document (4), U.S. Pat. No. 3,426,011.

Anionic groups of these cyclodextrins are in particular sulphopropyl or sulphoethyl ethers. These cyclodextrins having anionic properties are obtained by the action of a haloalkyl sulphonate on an activated cyclodextrin in alkoxide form. This reaction makes it possible to obtain statistically substituted products.

Sulphonated derivatives of linear monosaccharides have long been known, particularly from document (5), Carbohydrate Research, 22 (1972), pp. 23–35 by J. Lehmann and W. Weckerle, "Zuckersulfonsäuren"; document (6), M. Myano and A. Benson, J. Am. Chem. Soc., 84, 59, (1972), pp. 57–62, "The plant sulfolipid. VI. Configuration of the glycerol moiety"; document (7), R. Whistler and D. Medcalf, Archives of Biochemistry and Biophysics 105, 1964, p. 1–6 "Preparation of 6-deoxyamylose-6-sulfonic acid".

The processes for producing these sulphonated derivatives are generally long and complex.

The invention relates to novel derivatives of cyclomalto-oligosaccharides having anionic properties, which have at least one sulphonate group, having all the properties and advantages of known cyclodextrins with sulphate groups. The preparation process for the same is also simple.

According to a main feature of the invention, the sulphonated derivatives of cyclomalto-oligosaccharides are in accordance with the following formula (I):

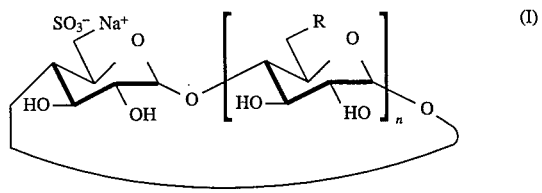

in which n is an integer from 2 to 50 and R represents —$SO_3^-Na^+$ or —OH, in which R can differ from one cycle to the next. In particular, n is 2 to 10.

The anionic groups can be arranged in a symmetrical or non-symmetrical manner on the oligosaccharide, as a function of the application thereof.

The cyclic sulphonated derivatives according to the invention have, as a result of the presence of one or more sulphonate groups, an increased solubility in water compared with their unsulphonated homologs. These groups also give a considerable stability to the derivatives and permit their orientation in an electric field.

Thus, they can be used as supports for substances or active principles and in particular as an encapsulating agent for ensuring the transport of these substances or active principles in water, where they are generally insoluble.

In addition, the cyclomalto-oligosaccharides according to the invention have the advantage, compared with natural $\beta$-cyclodextrins of being non-hemolytic, so that they can be used for forming intravenously injectable or ingestable medicaments.

The invention also relates to a support for active substances containing a derivative of formula (I).

The invention also relates to an original preparation process for the sulphonated derivatives. According to a main feature of this process, sodium sulphite is reacted on a halide of a corresponding cyclomalto-oligosaccharide, in the presence of a phase transfer agent, said halide having at least one halogen atom in the 6-position of a glucose cycle. The direct mycellization properties are used in this process.

The 6-halo-derivatives are obtained by known processes. Moreover, the exchange reaction of a halide for a sulphonate has long been known in organic chemistry.

The halide can be an iodide, a bromide or a chloride. It can be monohalogenated, partly halogenated or perhalogenated. The position of the halogens in the starting cyclomalto-oligosaccharide fixes the position of the sulphonate groups.

Advantageously, the reaction is performed in an aqueous medium, the phase transfer agent ensuring the dissolving of the halide of the cyclomalto-oligosaccharide, which is normally insoluble in water.

The use of one or more organic solvents such as dimethyl sulphoxide (DMSO), dimethyl fluoride (DMF), N-methyl pyrrolidone, to which water may be added, does not make it possible to obtain the sought product. Only the starting product or the 3,6-anhydro-D-glucose derivative occurs in the reaction medium.

A phase transfer agent or surfactant is a compound having a polar head and a sufficiently long hydrophobic chain leading to highly marked hydrophilic and lipophilic tendencies respectively. The dissolving of a small surfactant quantity in a polar or non-polar solvent leads to a significant reduction in the surface tension. Moreover, beyond certain characteristic concentration thresholds, the surfactant solutions are able to incorporate large quantities of compounds normally insoluble in the medium in question.

In order to favour the approach of the sulphite anion solubilized in water to the halo-sulphodextrins, use is preferably made of a surfactant with a polar head positively charged by a quaternary ammonium group. The hydrophobic part has alkyl groups with a chain having 2 to 15 carbon atoms.

The choice of the counterion or anion of the surfactant is important, because it must not compete with the sulphite anion in the halide-sulphite exchange reaction. Reference can be made to the sulphate, sulphite, acetate, chloride, bromide or iodide anion as a possible counterion for the surfactant.

Thus, as the mass transfer agent usable in the invention, reference can be made to hexadecyl trimethyl ammonium bromide or methyl trioctyl ammonium sulphate.

In order to avoid on the one hand the oxidation of the sulphite ion into sulphate in the acid medium and consequently the bringing about of the formation of 6-deoxy-D-glucose units on the starting halogenated cyclodextrin and on the other the formation of 3,6-anhydro-D-glucose units in the alkaline medium, the exchange reaction preferably takes place in a neutral or weak acid medium, i.e. at a pH from 4 to 8.

The process according to the invention has the advantage of being simpler than known processes for the preparation of sulphonated monosaccharide derivatives, like that described in document (7) for the formation of amylose or perhalogenated, linear malto-oligosaccharide.

The acid used can be organic or mineral. Thus, the reaction medium can be a sulphuric, sulphurous, hydrochloric, hydroiodic, bromhydric or acetic medium.

Other features and advantages of the invention can be better gathered from studying the following examples concerning the preparation of sulphonated derivatives given in an illustrative and non-limitative manner.

Preliminary Example: Preparation of the phase transfer solution.

4.2g (i.e. 0.1 mole/l) of methyl trioctyl ammonium chloride are dissolved in 500 ml of water and treated with 60g of basic resin of the Dowex® SBR OH⁻ type for 0.25 h. The resin is then removed by filtration and carefully rinsed with distilled water. The combined filtrates are neutralized by a 2N sulphuric acid solution. This neutralization is followed by potentiometry. The emulsion volume obtained is topped up to 1.51 and its pH adjusted to 6.5 by adding 1N soda solution. This stable surfactant emulsion is used directly in the operating procedures described hereinafter for the preparation of the sulphonated cyclomalto-oligosaccharide sodium salt.

EXAMPLE 1: Synthesis of the heptakis (6-deoxy-6-sulphonyl)cyclomalto-heptaose sodium salt.

To 120 ml of the aforementioned surfactant emulsion are added 900 mg (7.14 mmole) of sodium sulphite and 900 mg (3.31 mequiv) of heptakis (6-deoxy-6-iodo)-cyclomalto-heptaose prepared according to the operating procedure described by A. Gadelle and J. Defaye in document (8), Angew. Chem. Int. Ed. Engl., 30, pp. 78–80, 1991, "Selective halogenation at primary positions of cyclomalto-oligosaccharides and a synthesis of per-3,6-anhydro-cyclomalto-oligosaccharides".

The mixture is heated to 100° C. during 24 hours. After cooling, the reaction mixture is extracted by dichloromethane in two passages of 100 ml each. The organic fraction is brought to dryness (i.e. 4.2g) and also contains the surfactant, heptakis (6-deoxy-6-sulphonyl)-cyclomalto-heptaose.

To this organic residue is added 1 ml of DMSO and an organic mixture containing 250 ml of methanol, 150 ml of acetone and
1 ml of aqueous 4N soda solution. The cloudy solution obtained is then centrifuged at 5000 r.p.m. for 20 minutes. The sediments recovered are dissolved in distilled water and the filtered solution is lyophilized.

A NMR spectrum of the $^{13}$C reveals the presence of the heptakis (6-deoxy-6-sulphonyl)-cyclomalto-heptaose sodium salt. 700mg thereof are obtained, which corresponds to an 85% yield based on the starting halide.

This sodium salt has the following characteristics:

NMR of $^{13}$C (d and $D_2O$ with DMSO taken as the reference at 39.6 ppm), δppm: C-1 102.5; C-4 83.34; C-2, C-3, C-5 74.10, 73.31, 69.08; C-6 51.64.

$[\alpha]_D$=(c, $H_2O$)+76, melting point=+265° C.

The calculated microanalysis for $C_{42}H_{63}O_{49}S_7Na_7$ gives: C% 29.03; H% 3.36; S% 12.90; Na% 9.

The microanalysis found is: C% 29.00, H% 3.80; S% 12.65; Na% 7.8.

EXAMPLE 2: Synthesis of hexakis (6-deoxy-6-sulphonyl)-cyclomalto-hexaose sodium salt.

To 120ml of the above surfactant emulsion are added 900 mg (7.14 mmole) of sodium sulphite and 900 mg (3.31 mequiv) of hexakis (6-deoxy-6-iodo)-cyclomalto-hexaose, prepared as in document (8). The mixture is heated to 100° C. for 24 hours. After cooling, the reaction mixture is extracted by dichloromethane in two passages of 100 ml each. The organic fraction is brought to dryness (i.e. 4.2g) and also contains the surfactant, hexakis (6-deoxy-6-sulphonyl)-cyclomalto-hexaose.

To this organic residue is added DMSO and an organic mixture, as in Example 1. The cloudy solution obtained is then centrifuged as hereinbefore. The recovered sediments are dissolved in distilled water and the filtered solution is lyophilized.

A NMR spectrum of $^{13}$C reveals the presence of the hexakis (6-deoxy-6-sulphonyl)-cyclomalto-hexaose sodium salt. 653mg thereof are obtained, which corresponds to an 80% yield, based on the starting halide.

This sodium salt has the following characteristics:

NMR of $^{13}$C (d and $D_2O$ with DMSO used as the reference at 39.6 ppm), δppm: C-1 102.5; C-4 83.34; C-2, C-3, C-5 74.10, 73.31, 69.08; C-6 51.64.

$[\alpha]_D = (c, H_2O) + 75$, melting point = +258° C.

The calculated microanalysis for $C_{36}H_{54}O_{42}S_6Na_6$ gives: C% 29.03; H% 3.63; S% 12.90; Na% 9.

The microanalysis found is: C% 28.08; H% 3.9; S% 11.7; Na% 6.9.

EXAMPLE 3: Synthesis of heptakis (6-sulphonyl)-cyclomalto-heptaose sodium salt.

The 900 mg of heptakis (6-deoxy-6-iodo)-cyclomalto-heptaose of Example 3 are replaced by 750 mg of heptakis (6-bromo-6-deoxy)-cyclomalto-heptaose.

The product obtained has the same physical characteristics as that obtained from the corresponding iodine derivative of Example 3.

The sodium salts according to the invention can be used as a support for active substances and in particular as an encapsulating agent so as to transport them to target sites in the human body. These active substances are in particular neurotropes used in the treatment of epileptics, geriatrics and against tumours. The sodium salts can also be used for the transport of antihypertensive agents and diuretics, as well as AZT.

Their high solubility in water, their stability and their non-destruction of the walls of erythrocytes (due to their anionic groups) permit the venous injection of these active substances which have hitherto been insoluble in water.

We claim:

1. A sulphonated derivative of cyclomalto-oligosaccharide, in accordance with the following formula (I):

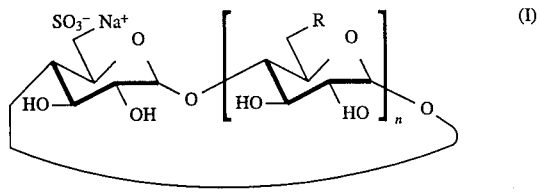

(I)

in which n is an integer from 2 to 50 and R represents $-SO_3^-Na^+$ or $-OH$, in which R can differ from one cycle to the next.

2. A derivative according to claim 1, wherein n is 2 to 10.

3. A derivative according to claim 1 or 2, wherein $R = -SO_3^-Na^+$ for all cycles and n is 5 or 6.

4. A process for the preparation of a sulphonated derivative according to claim 1, wherein sodium sulphite is reacted on a halide of a corresponding cyclomalto-oligosaccharide, in the presence of a phase transfer agent, said halide having at least one halogen atom in the 6-position of a glucose cycle.

5. A process according to claim 4, wherein the halide is an iodide or bromide.

6. A process according to claim 4 or 5, wherein the phase transfer agent has a polar head positively charged by an ammonium group and a hydrophobic part having an alkyl group negatively charged by a counterion which does not compete with the sulphite anion.

7. A process according to claim 4, wherein the phase transfer agent is methyl trioctyl ammonium sulphate.

8. A process according to claim 4 or 5, wherein the reaction of the sodium sulphite on the halide is performed at a pH from 4 to 8.

9. A support for active substances, wherein the support contains a sulphonated derivative according to any one of the claims 1 or 2.

10. A support according to claim 9, wherein the support is in the form of an encapsulating agent.

* * * * *